United States Patent [19]

Sandidge, Jr.

[11] Patent Number: Plant 6,190

[45] Date of Patent: May 31, 1988

[54] APPLE TREE: SANDIDGE VARIETY

[76] Inventor: Charles R. Sandidge, Jr., 5618 Entiat River Rd., Entiat, Wash. 98822

[21] Appl. No.: 852,542

[22] Filed: Apr. 16, 1986

[51] Int. Cl.[4] ..... A01H 5/03

[52] U.S. Cl. ..... Plt./35

[58] Field of Search ..... Plt./35

[56] References Cited

U.S. PATENT DOCUMENTS

P.P. 3,578 6/1974 Campbell ..... Plt. 35

P.P. 4,819 2/1982 Green ..... Plt. 35

P.P. 4,839 4/1982 Evans ..... Plt. 35

*Primary Examiner*—Robert E. Bagwill

*Attorney, Agent, or Firm*—Christensen, O'Connor, Johnson & Kindness

[57] ABSTRACT

A new variety of Red Delicious apple tree originating as a sport of the Red Chief Campbell Strain, exhibiting a characteristically solid red fruit stalk, a red midrib stripe that extends almost the entire length of the leaf blade, and advantageously exhibiting substantially earlier color formation than its parent.

2 Drawing Sheets

The subject plant is a new and distinct variety of Red Delicious apple tree that was discovered by Charles Ray Sandidge, Jr., originating as a whole tree sport of the Red Chief Campbell Strain, U.S. Plant Pat. No. 3,578, in the discoverer's orchard at Entiat, Wash. The subject apple tree has been fruited through three successive generations in the discoverer's orchard by budding and grafting, and has also been asexually reproduced in the Van Well Nursery orchard at Wentachee, Wash. Each successive generation has proved true to the original bud sport so as to establish the genetic stability of this new variety, for which the variety name "Sandidge" is proposed.

Figures 1A, 1B:
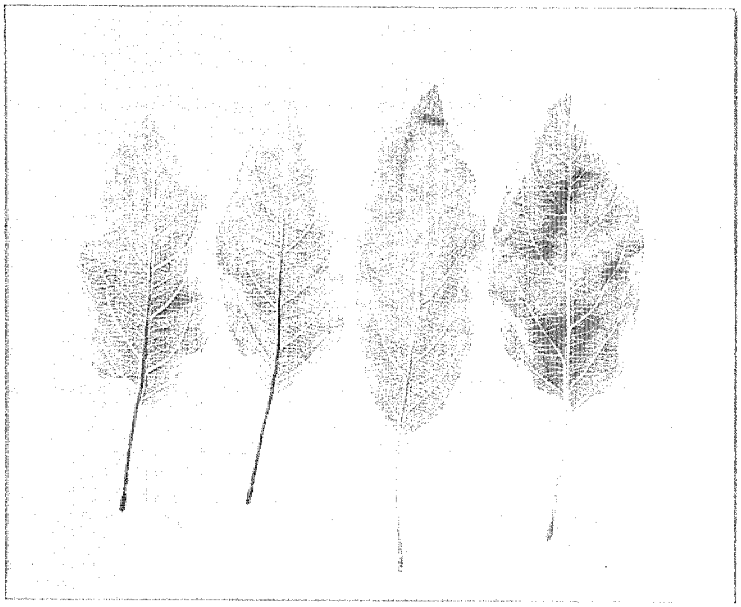

The following characteristics clearly distinguish the new variety from the Red Chief Campbell Strain parental stock:

Midrib: The underside of the main leaf vein on bearing and nonbearing trees of this new variety is intensely colored by a red stripe that extends from the petiole to about the top of the leaf blade. Red Chief Campbell Strain bears a similarly colored but much shorter midrib stripe. FIG. 1A shows how the midrib stripe on leaves of the subject tree extends through the petiole substantially to the distal tip of the leaf blade. In contrast, the midrib stripe in leaves of the parent stock (FIG. 1B) is confined to the petiole and proximal half of the leaf.

Figures 2A, 2B:
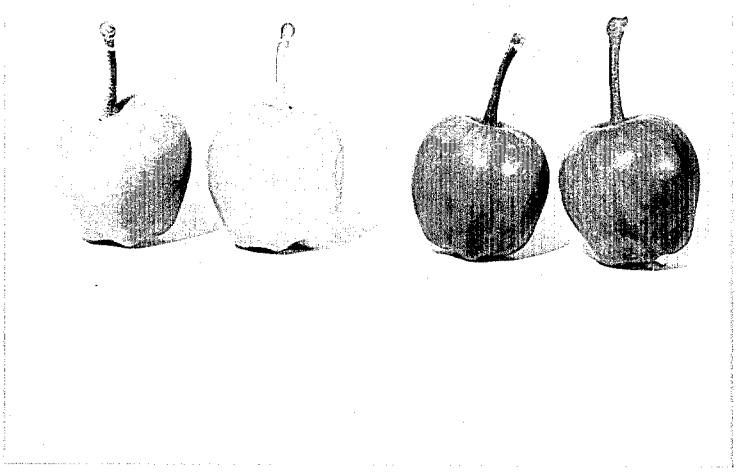

Pedicel: The fruit stalk of this new variety is solid red (FIG. 2A), in contrast to Red Chief which is identified by a distinctly striped stem color pattern (FIG. 2B). The stem of the new variety also tends to be slightly longer and thinner than that of the parent stock.

Figure 4:
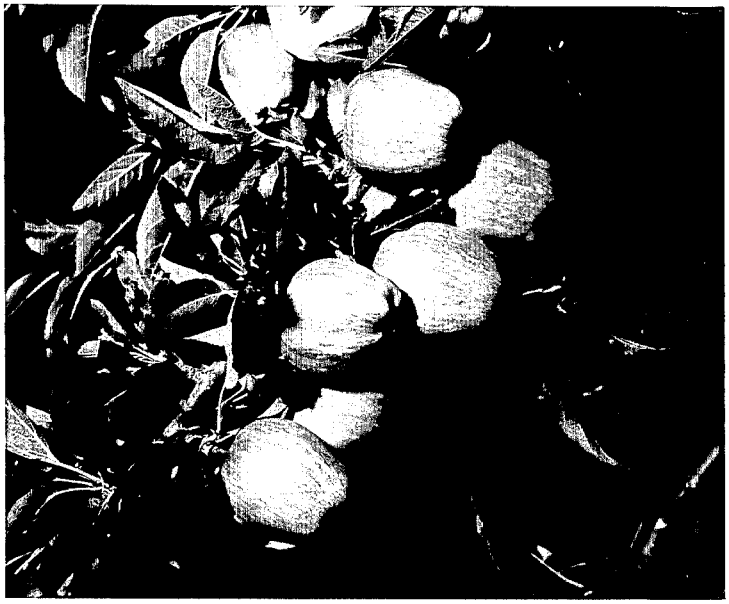
Figure 3:
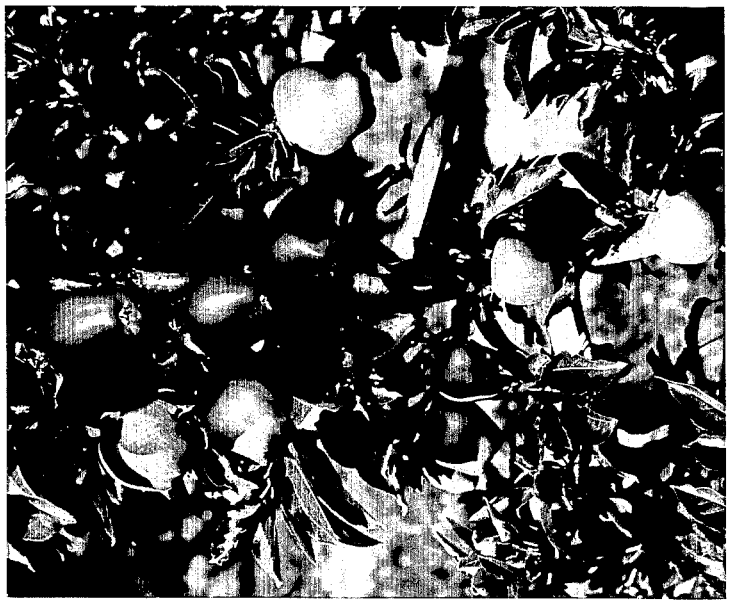

Early coloring: The new variety exhibits substantially earlier color formation than does Red Chief, on the order of eighteen days earlier in Chelan County, Wash., as shown in FIGS. 3 and 4. Specimens of the new variety (FIG. 3) and the parent stock (FIG. 4) were grown to similar size in adjacent rows, twenty feet apart, at the discoverer's orchard. Both specimens flowered at the end of April, and the onset and development of fruit coloration was monitored throughout the growing season. These photographs were taken in early August, showing the new variety to color earlier than Red Chief, which itself is known for early color development.

The new variety has also been grown alongside what are considered to be the next most similar varieties of apple tree: Oregon Spur II, Green Strain, U.S. Plant Pat. No. 4,819; and Scarlet Spur, Evans Strain, U.S. Plant Pat. No. 4,839. In earliness of color development the subject tree resembles Scarlet Spur, but Scarlet is a blush type coloring apple while the subject apple colors with a striped color pattern. The subject tree is distinguished from Oregon Spur II, Green Stain, by earlier coloring, by stem color, and by the colored midrib of its leaves.

The following description of the new variety is based on both the original and the asexually propagated trees.

TREE

Form: The tree is small and vigorous with an upright and open growth form. It bears regularly and is very productive. The tree appears to be as hardy as its parent. The trunk is stocky, with medium arc. Tree lenticels are few, medium in size, and raised. New growth, meaning one or two year-old wood, are of medium profusion, medium jointed, with dull, gray-green, smooth epidermis. The branching angle of the branches is substantially like its parent. Internodes are short.

Leaf: Leaves are medium in length and width, dark green, and thick. They are abruptly pointed and rugose with finely serrate margins. The petiole is medium in length and thickness. There is a distinctive red stripe on the underside of the petiole that characteristically extends substantially throughout the midrib of the leaf.

Flowers: In Washington State the average first opening date is April 28 and the average date of full bloom is May 1, as in its parent stock. Flowers are medium in size and white.

FRUIT

Shape: The fruit shape resembles that of its parent. Because of its desirably long and drawn-out shape with prominent calyx lobes, the fruit shape is considered "very typey." The form is very uniform with a slight tendency to ribbing to the five prominent points on the calyx. The basin end is very symmetrical, fairly narrow and rounded, with high shoulders. The average transverse diameter of the fruit is about 3 inches, and the axial diameter is about 3¼ inches. The calyx is open and the segments are very persistent with both inner and outer surfaces pubescent. The eye is medium in size and partially open. The stamens occur as one distinct whorl.

Skin: Fruit skin is thick, tough, smooth, and glossy. The conspicuous lenticels are small, circular, and slightly depressed, occurring relatively infrequently on the shoulder but more frequently toward the calyx. Their color is white to creamy white.

Skin Color: Ground color is an attractive yellow with overcolor that initiates very early as a prominent stripe from the stem to the calyx. The stripping gradually fills in with a bright red overcolor and covers the stripes. Color development is two to three weeks ahead of Red Chief Campbell Strain. At maturity the apple fruit is a very bright red color with a faint hint of an understripe showing through. The color as identified with Ridgeway's Color Standards and Nomenclature (1912) varies from Carime Plate 1 Sub. "1" to Bordeau Plate XII Sub. "K."

Flesh: The flesh is very juicy, firm and crisp, and white to creamy-white, tinged with red in the cortex near the skin vascular bundles and calyx tube. The core is symmetrical and fairly large. The bundles are conspicuous and yellowish in color with the core lines distinct and clasping. The calyx tube is pubescent and the stem of the funnel is rather long. The seed cells are open and distant and quite tough, with an average length of about ¾ inch. The flavor is mild and sweet and rather rich. The aroma is pronounced and good.

Seeds: The seeds are perfect, and a full complement of 10 usully develops. The seeds are about 5/16 inch long and 3/16 inch wide. Seed color is a distinct brown.

Pedicel: The pedicel is medium thick, pubescent, with an average length of about 1 inch. The stem is characteristically a solid red, comparable to Ridgeway's Violet Carime Plate XII Sub. "M."

Use: The fruit is a commercially marketable apple of best quality and is an excellent keeper.

The embodiment of the invention in which an exclusive property or privilege is claimed is defined as follows:

1. A new and distinct variety of apple tree, substantially as shown and described.

* * * * *